(12) United States Patent
Drent et al.

(10) Patent No.: US 7,026,473 B2
(45) Date of Patent: *Apr. 11, 2006

(54) PROCESS FOR THE CARBONYLATION OF PENTENENITRILE

(75) Inventors: Eit Drent, Amsterdam (NL); Willem Wabe Jager, Amsterdam (NL)

(73) Assignee: Shell Oil Company, Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/837,401

(22) Filed: Apr. 30, 2004

(65) Prior Publication Data

US 2004/0230071 A1 Nov. 18, 2004

Related U.S. Application Data

(63) Continuation of application No. 09/804,891, filed on Mar. 13, 2001, now Pat. No. 6,743,911.

(30) Foreign Application Priority Data

Mar. 14, 2000 (EP) .................................. 00200926
Mar. 14, 2000 (EP) .................................. 00200927

(51) Int. Cl.
 C07D 223/10 (2006.01)
 C07C 255/00 (2006.01)

(52) U.S. Cl. ...................................... 540/485; 558/441

(58) Field of Classification Search ................ 558/441; 540/485

See application file for complete search history.

(56) References Cited

U.S. PATENT DOCUMENTS

| | | | |
|---|---|---|---|
| 4,298,546 A | 11/1981 | McGill | 260/465.9 |
| 4,933,483 A | 6/1990 | Burke et al. | 558/353 |
| 4,950,778 A | 8/1990 | Burke et al. | 558/353 |
| 5,434,290 A | 7/1995 | Stahl et al. | 558/353 |
| 5,679,831 A | 10/1997 | Sielcken | 560/204 |
| 5,693,851 A | 12/1997 | Sielcken et al. | 560/207 |
| 5,780,623 A | 7/1998 | Guit et al. | 540/538 |
| 5,821,378 A | 10/1998 | Foo et al. | 558/338 |
| 5,869,738 A | 2/1999 | Pan et al. | 560/207 |
| 5,886,973 A | 3/1999 | Iida | 369/116 |
| 6,018,081 A | 1/2000 | Burke et al. | 568/451 |
| 6,077,955 A * | 6/2000 | Di Cosimo et al. | 546/245 |
| 6,156,934 A | 12/2000 | Suykerbuyk et al. | 568/12 |
| 6,346,640 B1 | 2/2002 | Slany et al. | 558/353 |

FOREIGN PATENT DOCUMENTS

| | | |
|---|---|---|
| DE | 198 40 253 A1 | 3/2000 |
| DE | 19840253 A1 * | 3/2000 |
| EP | 0495547 A2 | 7/1992 |
| EP | 0495548 A2 | 7/1992 |
| EP | 0729943 A2 | 9/1996 |
| EP | 1263713 B1 | 5/2004 |
| WO | WO 96/19434 | 12/1995 |
| WO | WO 97/30973 | 8/1997 |
| WO | WO 98/37063 | 2/1998 |
| WO | WO 98/42717 | 10/1998 |
| WO | 99/09040 | 2/1999 |
| WO | 99/21820 | 5/1999 |
| WO | 99/47528 | 9/1999 |

OTHER PUBLICATIONS

International Preliminary Examination Report for PCT/EP01/02903 of Jan. 28, 2002.

* cited by examiner

*Primary Examiner*—Paul A. Zucker
(74) *Attorney, Agent, or Firm*—Donald F. Haas

(57) ABSTRACT

Processes to prepare 5-cyanovaleric acid or its ester are provided, by carbonylation of a pentenenitrile, wherein pentenenitrile is reacted with carbon monoxide and water and/or an alcohol in the presence of a catalyst system. The catalyst system contains:

(a) a metal of Group VIII or a compound thereof and
(b) a bidentate phosphine, arsine and/or stibine ligand, wherein the bidentate ligand has the general formula (I):

$$R^1R^2\text{-}M^1\text{-}R\text{-}M^2\text{-}R^3R^4 \qquad (I)$$

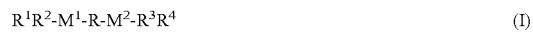

wherein $M^1$ and $M^2$ are independently P, As or Sb, R is a divalent organic bridging group, which bridging group comprises a chain of 3 to 5 atoms directly connecting the 2 phosphorus atoms, which chain consists of carbon atoms and optionally a nitrogen, oxygen or sulphur atom or a silano or dialkylsilicon group, which alkyl groups independently comprise from 1 to 4 carbon atoms, and $R^1$–$R^4$ represent the same or different optionally substituted tertiary alkyl groups, (c) an acid having a pKa less than 3, as measured at 18° C. in an aqueous solution.

ε-caprolactam is also prepared by reduction of 5-cyanovaleric acid or ester obtained above to 6-aminocaproic acid or ester, and then cyclisation of the 6-aminocaproic acid or ester to ε-caprolactam.

20 Claims, No Drawings

PROCESS FOR THE CARBONYLATION OF PENTENENITRILE

This is a continuation of Application Ser. No. 09/804,891 filed Mar. 13, 2001, now U.S. Pat. No. 6,743,911, the entire disclosure of which is hereby incorporated by reference.

BACKGROUND OF THE INVENTION

The invention relates to a carbonylation process of pentenenitrile to prepare 5-cyanovaleric acid or its ester in the presence of a catalyst system and to a process to prepare ε-caprolactam wherein such a carbonylation process is used.

Commercial processes for the preparation of ε-caprolactam use either phenol or cyclohexane as starting compounds. A disadvantage of these routes is that ammonium sulphate is produced as an unwanted by-product. Furthermore, these known processes include numerous process steps, which makes the preparation of ε-caprolactam a laborious and costly process. Thus, in the field of preparing ε-caprolactam there is a great need for a new route based on butadiene.

In recent patent literature, a butadiene based preparation of ε-caprolactam is described wherein first a pentenoate ester is prepared by carbonylation of butadiene, which in turn is reacted to 5-formylvalerate ester in a hydroformylation step. The 5-formylvalerate ester is subsequently converted to 6-aminocaproic acid or its ester in a reductive amination step. 6-aminocaproic acid or its ester is subsequently reacted to ε-caprolactam upon heating in an aqueous medium. According to U.S. Pat. No. 5,693,851, which describes a palladium catalysed carbonylation of butadiene at 140° C., the best selectivity to methyl 3- and 4-pentenoate ester is about 93%. According to U.S. Pat. No. 6,018,081, which describes a rhodium catalysed hydroformylation of methyl pentenoate ester, the best selectivity to methyl 5-formylvalerate ester is 81%. According to EP-A-729943 and WO-A-9837063, a 100% conversion of methyl 5-formylvalerate to ε-caprolactam is achievable in the reductive amination and cyclisation steps. Based on butadiene the overall selectivity is thus at most about 75%. This means that 25% of the starting butadiene is converted to by-products. It will be clear that this overall selectivity will have to be significantly improved for a commercial application.

DE-A-19840253 describes the possibility of a process to prepare caprolactam starting from 5-cyanovaleric acid and its esters. Through hydrogenation to 6-aminocaproic acid, respectively 6-aminocaproic ester and elimination of the water or alcohol caprolactam can be obtained.

DE-A-19840253 further relates to a process to prepare cyanovaleric acids or esters by reacting pentenenitril with water or an alkanol and carbon monoxide in the presence of a catalyst system comprising a palladium (II) compound, a bidentate diphosphine and a source of anions. On page 3, lines 29–36, DE-A-19840253 mentions an extensive list of possible bidentate diphosphine ligands, including for example 1,2-bis(di-n-butylphosphino)ethane, 1,3-bis(dimethylphosphino)propane, 1,3-bis(di-isopropyl-phosphino)propane and 1,2-bis(di-cyclohexylphosphino)ethane, as well as 1,3-bis(di-tert-butylphosphino)propane. In addition DE-A-19840253 mentions, on page 4, lines 55 to 62, a whole range of possible sources of anions, of which weak organic acids with a pKa of 3.5 or more, such as 9-anthracenecarboxylic acid, are preferred.

In its examples DE-A-19840253 describes the preparation of methyl 5-cyanovalerate by reacting 3-pentenenitril with methanol and carbon monoxide in the presence of Palladium (II)acetate, 9-anthracenecarboxylic acid, and 1,2-bis(dicyclohexylphosphino)ethane or a mixture of 1,2-bis(1,5-cyclooctylenephosphino)ethane and 1,2-bis(1,4-cyclooctylenephosphino)ethane at a temperature of 150° C. At conversions lying in the range from 40 to 90%, selectivities to the desired methyl 5-cyanovalerate in the range from 70 to 72% were obtained.

U.S. Pat. No. 4,950,778 describes a process to prepare 5-cyanovaleric acid by reacting 3-pentenenitrile with water and carbon monoxide in the presence of a cobalt catalyst at a pressure of 136 bar and a temperature of 200° C. At a conversion of 87.4%, the selectivity to the undesired branched $C_6$ acids was 9.1% and to the undesired valeronitril was 9.6%.

U.S. Pat. No. 5,434,290 describes a process to prepare methyl 5-cyanovalerate by reacting 3-pentenenitrile with methanol and carbon monoxide in the presence of a cobalt catalyst at a pressure of 200 bar and a temperature of 160° C. At a conversion of 66%, the selectivity to the desired methyl 5-cyanovalerate was about 89%.

Some of the disadvantage of the above processes are the high operating pressure and/or temperature, the use of high concentrations of cobalt carbonyl compounds and/or the low selectivity at a relatively low conversion.

U.S. Pat. No. 5,679,831 describes the carbonylation of methyl 3-pentenoate to dimethyl adipate by reacting the methyl-3-pentenoate with methanol and carbon monoxide in the presence of a catalyst system consisting of palladium, 1,1'-bis(diisopropylphosphino)ferrocene and p-toluene sulphonic acid at a pressure of 60 bar and a temperature of 130° C. At 99% conversion, a 83% selectivity to dimethyl adipate was obtained. Another experiment performed at 90° C. illustrated a selectivity of 84% to adipate at a 71% conversion of pentenoate. All experiments were performed starting with pentenoate and with an acid to palladium molar ratio of above 10. Pentenenitrile is mentioned as a possible substrate instead of pentenoate. However if pentenenitrile is used instead of methyl-3-pentenoate using the same ligand and under the conditions of the examples, no catalyst activity is observed. Another disadvantage is that because of the high acid concentration the reaction mixture is corrosive and more ligand degradation results due to quartanization of the phosphine compound with the acid and the olefinic compound.

EP-A-495548 describes the carbonylation of propene by reacting propene with methanol and carbon monoxide in the presence of palladium, 1,3-bis(di-tert.butylphosphino)propane and methylsulphonic acid at a pressure of 30 bar and a temperature of 60° C. The selectivity to the desired linear methylbutanoate was 86%.

SUMMARY OF THE INVENTION

A process for preparing a 5-cyanovaleric acid or its ester is provided, comprising reacting pentene-nitrile with carbon monoxide and water and/or an alcohol in the presence of a catalyst system, comprising
(a) a source of Group VIII metal and
(b) a bidentate phosphine, arsine and/or stibine ligand, wherein the bidentate ligand has the general formula (I):

$$R^1R^2\text{-}M^1\text{-}R\text{-}M^2\text{-}R^3R^4 \qquad (I)$$

wherein $M^1$ and $M^2$ are independently P, As or Sb, R is a divalent organic bridging group, which bridging group comprises a chain of 3 to 5 atoms directly connecting the 2 phosphorus atoms, which chain consists of carbon atoms and optionally a nitrogen, oxygen or sulphur atom or a silano or dialkylsilicon group, which alkyl groups independently comprise from 1 to 4 carbon atoms, and $R^1$–$R^4$ represent the same or different optionally substituted tertiary alkyl groups, (c) an acid having a pKa less than 3, as measured at 18° C. in an aqueous solution.

Also provided is a process to prepare ε-caprolactam comprising reducing 5-cyanovaleric acid or ester obtained above to 6-aminocaproic acid or ester, and then cyclisation of the 6-aminocaproic acid or ester to ε-caprolactam.

DETAILED DESCRIPTION OF THE INVENTION

The invention aims to provide a process for the preparation of 5-cyanovaleric acid or its esters in a high yield and at moderate process conditions. A high yield process to prepare 5-cyanovaleric acid or its ester is provided by carbonylation of a pentenenitrile, wherein pentenenitrile is reacted with carbon monoxide and water and/or an alcohol in the presence of a catalyst system, comprising (a) a metal of Group VIII or a compound thereof and
(b) a bidentate phosphine, arsine and/or stibine ligand, wherein the bidentate ligand has the general formula (I):

wherein $M^1$ and $M^2$ are independently P, As or Sb, R is a divalent organic bridging group, which bridging group comprises a chain of 3 to 5 atoms directly connecting the 2 phosphorus atoms, which chain consists of carbon atoms and optionally a nitrogen, oxygen or sulphur atom or a silano or dialkylsilicon group, which alkyl groups independently comprise from 1 to 4 carbon atoms, and $R^1$–$R^4$ represent the same or different optionally substituted tertiary alkyl groups, (c) an acid having a pKa less than 3, as measured at 18° C. in an aqueous solution.

It has been found that with the process according to the invention a 5-cyanovaleric acid or ester can be obtained in a high yield under process conditions which are mild with respect to operating pressure and/or temperature.

In view of DE-A-19840253 it was unexpected that the carbonylation of pentenenitrile in the presence of a certain selection of the bidentate diphoshines specified under b) in combination with the acid specified under c) would result in such a high yield of linear product. Particularly in view that the use of some of the bidentate diphosphines mentioned in DE-A-19840253 in the process in a similar process gave very poor results, as shown in the examples below.

In view of EP-A-495548 it was unexpected that starting from pentenenitrile, a higher selectivity to linear products can be obtained than when starting from a more simple molecule like propene as illustrated in the publication. In view of U.S. Pat. No. 5,679,831, it is unexpected that when using a compound, cited as one of the less preferred starting compounds, a higher yield is obtained than those disclosed in such publication for dimethyl adipate.

The process is especially advantageous because it can be performed at a relatively low temperature. A problem often encountered with the use of catalyst systems comprising palladium, phosphines and acids is that the catalyst stability becomes too low for commercial application at elevated temperatures, especially above 120° C. Because the catalyst has a commercially acceptable activity at temperatures of below 120° C., and especially below 110° C., less catalyst will be consumed by the process.

In addition, the process according to the invention can advantageously be used in a process to prepare ε-caprolactam. E-Caprolactam can be obtained with a high selectivity based on pentenenitrile, which in turn can be prepared from butadiene in a high selectivity, >95% according to U.S. Pat. No. 5,821,378. It has now been found that carbonylation of pentenenitrile to 5-cyanovaleric acid or ester can be performed with a 96% selectivity to 5-cyanovalerate ester at 96% conversion of pentenenitrile. Hydrogenation to 6-aminocaproic acid, respectively 6-aminocaproic ester and elimination of the water or alcohol to obtain ε-caprolactam are, with respect to their chemistry, very comparable with the reductive amination and cyclisations steps as exemplified in EP-A-729943 and WO-A-9837063. Therefore, a comparable selectivity of about 100% may be assumed for these steps. Thus by using pentenenitrile, as obtained at a 95% selectivity from butadiene, in the present process an overall selectivity of about 90%, based on butadiene, to ε-caprolactam is possible.

Among the metals of Group VIII, cobalt, nickel, palladium, rhodium and platinum may be mentioned. Of these, palladium is preferred. As source of Group VIII metal, hereinafter further exemplified as source of palladium, metallic palladium or, preferably, a palladium compound may be used, in particular a palladium salt. The palladium compound used in the process of the invention may be provided in the form of a palladium complex of the specified ligand according to formula (I). It may also conveniently be generated in situ by adding a source of palladium and sources of the ligand to the reaction. Suitable sources of palladium include Pd(0)(dibenzylaceton)$_2$, palladium carboxylates, such as palladium acetate, propionate, butyrate or benzoate, and palladium salts of mineral acids. Further sources include palladium complexes such as palladium acetylacetonate, tetrakis(triphenylphosphine)palladium and bis(tri-otolylphosphine)palladium acetate. Palladium may be used in a heterogeneous form such as, for example, loaded on an ion exchange resin.

Preferably palladium salts of alkanoic acids are used, in particular alkanoic acids with up to 12 carbon atoms, for example acetic acid, propionic acid or trifluoroacetic acid.

In the bidentate of formula I, $M^1$ and $M^2$ are preferably the same and in particular they both represent phosphorus atoms.

For being capable of bidentate coordination to the preferred palladium atom, the bidentate diphosphine ligands of the catalyst system should be free of substituents offering steric hindrance to a bidentate coordination mode. In particular, the divalent bridging group R should be free of substituents offering steric hindrance. The bridging group R is preferably an organic divalent group comprising 3 to 20 atoms. Preferably the chain of atoms connecting the two phosphorus atoms does not contain terminal heteroatoms. More preferably the bridging group consists only of carbon atoms. Examples of possible bridging groups are substituted or unsubstituted divalent aryl groups, for example dixylyl. Another preferred group of bridging groups are C3–C5 alkylene groups: trimethylene, tetramethylene and pentamethylene of which trimethylene is most preferred.

The bridging group may optionally be substituted by one or more substituents, provided that the substituents do not offer steric hindrance to the bidentate ligand coordination mode. Examples of possible substituents are alkyl groups, e.g. of 1 to 4 carbon atoms.

In the present specification the alkyl groups represented by $R^1$ to $R^4$ include cyclic structures. $R^1$ and $R^2$ and/or $R^3$ and $R^4$ may form one cyclic structure, optionally containing heteroatoms. More preferably $R^1$ and $R^2$ and/or $R^3$ and $R^4$ represents a bivalent radical that together with the phosphorus atom to which it is attached is an alkyl substituted 2-phosphatricyclo[3.3.1.1{3,7}]decyl group or a derivative thereof in which one or more of the carbon atoms are replaced by heteroatoms. Preferably the ligand comprising the alkyl substituted 2-phospha-tricyclo[3.3.1.1{3,7}]decyl group is a compound according to Formula II, wherein $R^5$ are alkyl groups of 1–6 carbon atoms, preferably methyl. Examples of such ligands and their preparation are described in more detail in WO-A-9842717 and U.S. Pat. No. 6,156,934 which disclosures are hereby incorporated by reference.

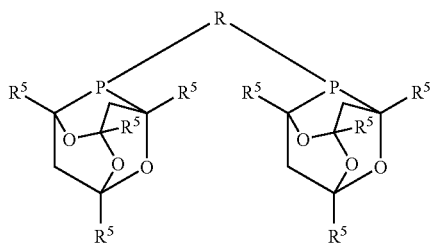
(II)

Preferably the tert.alkyl groups are non-cyclic tert. alkyl groups. Examples of suitable non-cyclic tertiary alkyl groups are tertiary butyl, tertiary pentyl, 1-ethyl-1-methylpropyl 1,1-dimethylbutyl and 1-ethyl-1-methylbutyl groups. Preferably the groups $R^1$ to $R^4$ represent the same tertiary alkyl groups, most preferably $R^1$ to $R^4$ are tert.butyl groups.

Examples of possible ligands are 1,4-bis(di-tertiarybutylphosphino)butane, 1,5-bis(di-tertiarybutylphosphino)pentane, 1,3-bis[(di-tert-pentyl)phosphino]propane, 1,3-bis[(1-ethyl-1-methylpropyl)phosphino]propane, 1,3-P,P'-di(2-phospha-1,3,5,7-tetramethyl-6,9,10-trioxatricyclo[3.3.1.1{3.7}]decyl)propane (DPA3), 1,4-P,P'-di(2-phospha-1,3,5,7-tetramethyl-6,9,10-trioxatricyclo[3.3.1.1{3.7}]decyl)butane, 1,2-bis[(di-tert-pentyl)phosphinomethyl]benzene.

Particularly preferred bidentate ligands are: 1,3-bis(di-tertiarybutylphosphino)propane and 1,2-bis(di-tertiarybutylphosphinomethyl)benzene, wherein the bridging group may be optionally further substituted as described above.

The acid having a pKa below 3.0 preferably has a non-coordinating anion, by which is meant that little or no covalent interaction takes place between the palladium and the anion. Typical examples of such anions are $PF_6-$, $SbF_6-$, $BF_4-$ and $ClO_4-$. Preferred acids are for example, sulfonic acids and acids that can be formed, possibly in situ, by interacting a Lewis acid such as, for example $BF_3$, $AsF_5$, $SbF_5$, $PF_5$, $TaF_5$ or $NbF_5$ with a Broensted acid such as, for example, a hydrohalogenic acid, in particular HF, fluorosulfonic acid, phosphoric acid or sulfuric acid. Specific examples of acids of the latter type are fluorosilicic acid, $HBF_3$, $HPF_6$ and $HSbF_6$. Examples of suitable sulfonic acids are fluorosulfonic acid and chlorosulfonic acid and the hereinafter specified sulfonic acids. A preferred group of acids having a pKa below 3.0 has the general formula III

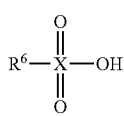
(III)

wherein X represents a sulphur or a chlorine atom and, if X represents a chlorine atom, $R^6$ represents an oxygen atom and, if X represents a sulphur atom, $R^6$ represents an OH group or a hydrocarbon group, for example an alkyl or aryl group, which can either be substituted or unsubstituted. Examples of suitable acids of the general formula III are perchloric acid, sulfuric acid, 2-hydroxypropane-2-sulfonic acid, p-toluenesulfonic acid, tert.butyl sulfonic acid, methyl sulfonic acid. The acid of the general formula III can also be an ion exchanger containing sulfonic acid groups, such as, for example, AMBERLITE 252H ("AMBERLITE" is a trade name). In that case, the hydrocarbon group $R^6$ represents a polymeric hydrocarbon group substituted with sulfonic acid groups such as, for example, a polystyrene group.

Another possible acid is according to the following general formula IV

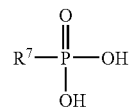
(IV)

wherein $R^7$ can be an —OH group or a hydrocarbon group, for example an alkyl or aryl group, which can either be substituted or unsubstituted. Examples are phosphoric acid, methyl phosphonic acid, phenyl phosphonic acid.

When the hereinbefore stated acids are used in the process according to the invention, the anions of the acids can be considered to be non-coordinating. The molar ratio of acid and metal (a) is preferably between 1:1 and 10:1 and more preferably between 1:1 and 5:1.

Since halide ions can be corrosive, the source of palladium in the catalyst systems of the invention is preferably not a halide or a compound generating halide ions. Small amounts of halide however may be advantageously present. Optionally other promoters may be present.

Conveniently the catalyst system of the invention is obtained by combining in a separate step, preceding the carbonylation reaction, the source of palladium and the bidentate ligand of formula I. Suitably the palladium compound, as exemplified hereinbefore, is dissolved in a suitable solvent, and subsequently admixed with the bidentate. The molar ratio between the bidentate ligand and the metal (a) is preferably in the range of 1:1 to 5:1 and, more preferably, in the range of 1:1 to 3:1. The possibility of applying these low molar ratios is advantageous, as it avoids the use of an excess of bidentate ligand and hence minimises the consumption of these usually expensive compounds.

The amount of catalyst used in the process is not critical. Good results are obtained when the amount of Group VIII metal is in the range of about $10^{-7}$ to about $10^{-1}$ gram atom per mole of pentenenitrile. Preferably this amount is in the range of about $10^{-5}$ to about $5.10^{-2}$ gat per mole.

If the carbonylation process is carried out in the presence of water, the product obtained will be 5-cyanovaleric acid. By-products will be mainly small amounts of branched cyano acids. 5-cyanovaleric acid is preferably obtained by hydrolysis of the 5-cyanovalerate ester as obtained by the process according to the invention.

In the process according to the invention, 5-cyanovaleric esters may be obtained directly, if the carbonylation is carried out in the presence of an alcohol. Suitable alcohols include aliphatic mono alcohols, in particular those having from 1–6 carbon atoms per molecule such as methanol, ethanol, propanol, butanol, isopropanol, phenol and dihydric alcohols such as ethylene glycol and 1,3-propane diol. Methanol is in particular preferred. When a 5-cyanovalerate ester is the desired product, the presence of water is preferably avoided. More preferably the process is performed in the presence of a water scavenger, for example trimethyl ortho formate.

The amount of alcohol or water is not critical. The mol ratio water or alcohol to pentenitrile may range from about equimolar to an excess of water or alcohol. Optionally the alcohol or water may serve as reaction solvent as well, although, if desired, separate solvents may also be used.

Additional solvents, if present, are preferably compounds which weakly co-ordinate with the palladium compound. Examples of suitable solvents are acetonitrile, ethanol, acetone, acetylacetone, toluene, sulfolane, and ethers, for example dimethyl ether of diethylene glycol, anisole diphenyl ether.

The carbonylation reaction according to the invention is carried out at moderate temperatures and pressures. Suitable reaction temperatures are in the range of about 50–250° C., preferably in the range of about 80–125° C. The reaction pressure is usually at least atmospheric. Suitable pressures are in the range of about 1 to about 100 bar, preferably in the range of about 5 to about 50 bar.

The carbon monoxide required for the reaction may be supplied in substantially pure form, or contaminated with in general minor amounts of inert compounds such as nitrogen, hydrogen and the like.

The process may be carried out in batch operation or continuously. In embodiments relating to continuous operation of the process, products are conveniently isolated from the catalyst system by means of distillation, preferably in a wiped film evaporator. Alternatively the products can be stripped from the reaction mixture with the aid of a gas.

The starting pentenenitrile may be a 2-, 3- or 4-pentenenitrile or their mixtures. It has been found that from all these starting compounds a high selectivity to linear products is obtained with the process according to the invention. Pentenenitrile may be advantageously be obtained by a process as described in for example U.S. Pat. No. 4,298,546 and U.S. Pat. No. 5,821,378 starting from butadiene and hydrogen cyanide.

The 5-cyanovaleric acid or ester can be used as an intermediate to prepare adipic acid or its ester. Adipic acid can be obtained by esterfication of the cyano group. Adipic acid is a precursor to Nylon-6.6. The other precursor to Nylon-6.6 is 1,3 di-cyanopropane which can be prepared from pentenenitrile. The present process therefore provides a manufacturer of Nylon-6.6 or its precursors a favourable route to adipic acid from a precursor which is already used to prepare 1,3 di-cyanopropane.

The 5-cyanovaleric acid or ester prepared according to the process of the invention can further be advantageously used in a process to prepare ε-caprolactam.

This invention thus also provides a process to prepare ε-caprolactam from pentenenitrile, comprising:
(i) carbonylation of pentenenitrile to 5-cyanovaleric acid or ester according to the process described herein above;
(ii) reduction of 5-cyanovaleric acid or ester as obtained in step (i) to 6-aminocaproic acid or ester,
(iii) cyclisation of the 6-aminocaproic acid or ester to ε-caprolactam.

The 5-cyanovaleric acid or ester as obtained in step (i) can be separated (or recovered) from the homogeneous catalyst system by for example distillation, extraction, phase separation or crystallisation, of which distillation is preferred. The catalyst system is advantageously re-used in the carbonylation reaction.

Even though a high selectivity is achieved in step (i) some by-products are formed. These by-products can for example be separated from the 5-cyanovaleric acid or ester by means of distillation or by one of the above mentioned techniques. A problem, however, can be that it can be difficult to separate the desired linear product from the branched products which are formed as by-product by means of distillation. In an advantageous embodiment therefore a mixture of branched and linear carbonylation products as obtained in step (i) is used in step (ii) and optionally also in step (iii). This further advantageously reduces the amount of purification steps after step (i). Because after step (iii) a rigorous purification of ε-caprolactam will take place, it is advantageous to combine these purification steps (recovering steps) with the separation of the by-products of the carbonylation.

This is especially possible with the present process because the content of by-products is low when compared to the state of the art routes to ε-caprolactam. The embodiment is further especially advantageous when 5-cyanovaleric acid is the product obtained in step (i). In view of their close boiling points it is not simple to separate the branched compounds from the desired 5-cyanovaleric acid. By not separating these acids in step (i), but instead further processing them as a mixture in steps (ii) and (iii) a more simple process is obtained. Separating the ε-caprolactam from the resulting branched lactams after step (iii) can be simply performed by for example crystallization or distillation.

Optionally the homogeneous catalyst used in step (i) is separated (removed) from the reaction mixture after step (ii).

Step (ii) can be performed by known reducing techniques. In this step hydrogen is contacted with the cyano compound obtained in step (i) in the presence of a reducing catalyst, suitably Cu or a Group VIII metal as for example Pt, Pd, Ni, Co, Ru, or Fe. This catalyst can be a homogeneous catalyst, for example, the catalyst used in step (i). Preferably a heterogeneous catalyst is used. Examples of reducing catalysts are Raney Ni, Raney Cobalt, and Co/Cu catalysts.

Step (iii) is suitably performed in a suitable solvent under conditions effective for cyclisation, preferably at an elevated temperature. Suitable solvents are water, high boiling hydrocarbons and alcohols, preferably the corresponding alcohol of the 6-aminocaproate ester. Preferably water is used as the solvent and 6-aminocaproic acid is used as the starting compound in step (iii) as for example described in U.S. Pat. No. 5,780,623 which disclosure is hereby incorporated by reference. The temperature is preferably between about 280 and about 400° C. If a 5-cyanovalerate ester is obtained in step (i) it may therefore be advantageous to first hydrolyse this compound to its corresponding acid prior to the reduction step (ii) or the cyclisation step (iii). Alternatively, the hydrogenated product of step (ii), i.e. 6-aminocaproic acid or its ester may be reacted to ε-caprolactam in the presence of super heated steam at a temperature of between from about 270 and to about 350° C. and a pressure of between about 5 and about 20 bar as exemplified in WO-A-9837063 which disclosure is hereby incorporated by reference.

The invention is illustrated by the following non-limiting examples.

EXAMPLES 1–9 AND COMPARATIVE EXAMPLES A–D

Examples 1–9 and comparative examples A–D were carried out in a magnetically stirred 250 ml Autoclave (Hastelloy C, trade mark). The autoclave was charged with methanol, and an optional solvent, in the amounts given, and 20 ml of 3-pentenenitrile, 0.25 mmol palladium(II) acetate, the selected phosphine and the acid in the amounts given. The Palladium acetate/phosphine were charged under a nitrogen atmosphere. After closure of the autoclave it was evacuated, whereupon 60 bar of CO was supplied. The autoclave was heated to the desired temperature. The initial rate of carbonylation was determined from the pressure decrease per time unit during the first hour of reaction. After a total reaction time of 10 hours the autoclave was cooled to room temperature and slowly depressurized thereafter. The selectivities, linearity of cyano-ester products and conversion were determined by gas liquid chromatographic analysis of the reaction products. See Table 1 for solvents, amounts, conditions and results.

EXAMPLE 10

Example 1 was repeated except that 0.6 mmol of 1,3-P,P'-di(2-phospha-1,3,5,7-tetramethyl-6,9,10-trioxatricyclo[3.3.1.1{3.7}decyl)propane (DPA3) was used as the ligand in the presence of 0.5 mmol $CH_3SO_3H$, 10 ml pentenenitrile and 40 ml methanol at 115° C. The initial rate (mol/mol/hr) was 100. The conversion was 70% after 10 hours. The selectivity to cyano-esters was 98%. The linearity was 88%.

EXAMPLE 11

Example 1 was repeated except that the autoclave was charged with 10 ml methanol, 40 ml anisole, 20 ml of 2-pentenenitrile, 0.25 mmol palladium(II) acetate, 0.6 mmol 1,3 bis(di-tert-butylphosphino)propane and 2 mmol tert-butylsulphonic acid. The Palladium acetate/phosphine were charged under a nitrogen atmosphere. After closure of the autoclave it was evacuated, whereupon 60 bar of Co was supplied. The autoclave was heated to 125° C. The initial rate (mol/mol/hr) was 200. The conversion was 74% after 4 hours. The selectivity to cyano-esters was 98%. The linearity was 92.5%.

| Ex. | Ligand (mmol) | acid (mmol) | reaction medium (ml) | temp. (° C.) | initial rate (mol/mol/hr) | conversion (%) | selectivity to cyano-esters (mol %) | linearity (mol %)(1) |
|---|---|---|---|---|---|---|---|---|
| 1 | 1,3 bis(di-tert-butylphosphino)propane (0.6) | $CH_3SO_3H$ (2) | $CH_3OH$ (40) | 115 | 200 | 85 | 98 | 93 |
| A | 1,3 bis(di-iso-propylphoshino)propane (0.6) | " | " | 115 | trace | <2 | — | — |
| 2 | 1,3 bis(di-tert-butylphosphino)propane (0.6) | " | " | 100 | 300 | 94 | 98 | 93 |
| 3 | 1,3 bis(di-tert-butylphosphino)propane (0.6) | $CH_3SO_3H$ (1) | " | 100 | 350 | 84 | 98 | 93 |
| 4 | 1,3 bis(di-tert-butylphosphino)propane (0.6) | t-$BuSO_3H$(2) | " | 100 | 350 | 95 | 98 | 94 |
| 5 | 1,3 bis(di-tert-butylphosphino)propane (0.6) | " | " | 90 | 250 | 87 | 98 | 94 |
| 6 | 1,3 bis(di-tert-butylphosphino)propane (0.6) | " | " | 125 | 400 | 96 | 98 | 93 |
| 7 | 1,2 bis(di-tert-butylphosphino)ethane (0.6) | " | " | 100 | <10 | 5 | 95 | 88 |
| 8 | 1,3 bis(di-tert-butylphosphino)propane (0.6) | " | $CH_3OH$ (10), anisole (30) | 100 | 400 | 96 | 98 | 96 |
| B | 1,3 bis(di-cyclohexylphosphino)propane (0.6) | " | $CH_3OH$ (10), anisole (30) | 100 | trace | <2 | — | — |
| C | 1,1' bis (di-isopropylphosphino)ferrocene (0.6) | " | $CH_3OH$ (10), anisole (30) | 100 | trace | <2 | — | — |
| 9 | 1,2-bis(di-tert-butylphosphino-methyl)benzene (0.6) | $CH_3SO_3H$ (1) | $CH_3OH$ (10), anisole (30) | 100 | 150 | 60 | 98 | 98 |
| D | tri-tertbutyl phoshine (monophosphine) (0.6) | " | $CH_3OH$ (10), anisole (30) | 100 | trace | <1 | — | — |

(1) linearity is the mol percentage of 5-cynaovalerate ester relative to all cyano-esters.

Note: Pentenentrile composition at intermediate conversions show a mixture of cis+trans-2-pentenenitriles, and cis+trans 3-pentenenitriles showing that all isomers can be converted to 4 cyano-methyl pentanoate.

We claim:

1. A process for preparing a 5-cyanovaleric acid or its ester comprising reacting pentenenitrile with carbon monoxide and water and/or an alcohol in the presence of a catalyst system, comprising
   (a) a source of Group VIII metal and
   (b) a bidentate phosphine, arsine and/or stibine ligand, wherein the bidentate ligand has the general formula (I):

$$R^1R^2\text{-}M^1\text{-}R\text{-}M^2\text{-}R^3R^4 \qquad (I)$$

wherein $M^1$ and $M^2$ are independently P, As or Sb, R is a substituted or unsubstituted divalent organic aryl bridging group, which bridging group comprises a chain of 3 to 5 atoms directly connecting $M^1$ and $M^2$, which chain consists of carbon atoms, and $R^1$–$R^4$ represent the same or different optionally substituted tertiary alkyl groups,
   (c) an acid having a pKa less than 3, as measured at 18° C. in an aqueous solution.

2. The process of claim 1 wherein the Group VIII metal is palladium.

3. The process of claim 1 wherein the molar ratio between the ligand (b) and the metal (a) is in the range of 1:1 to 5:1.

4. The process of claim 3 wherein the Group VIII metal is palladium.

5. The process of claim 1 wherein the reaction is carried out at a temperature in the range of about 80 to about 125° C.

6. The process of claim 2 wherein the reaction is carried out at a temperature in the range of about 80 to about 125° C.

7. The process of claim 1 wherein the molar ratio of acid compound (c) and metal (a) is between 1:1 and 5:1.

8. A process for preparing ε-caprolactam comprising:
   (i) reacting pentenenitrile with carbon monoxide and water and/or an alcohol in the presence of a catalyst system, comprising
   (a) a source of Group VIII metal,
   (b) a bidentate phosphine, arsine and/or stibine ligand, wherein the bidentate ligand has the general formula (I)

$$R^1R^2\text{-}M^1\text{-}R\text{-}M^2\text{-}R^3R^4 \qquad (I)$$

wherein $M^1$ and $M^2$ are independently P, As or Sb, R is a substituted or unsubstituted divalent organic aryl bridging group, which bridging group comprises a chain of 3 to 5 atoms directly connecting $M^1$ and $M^2$, which chain consists of carbon atoms, and $R^1$–$R^4$ represent the same or different optionally substituted tertiary alkyl groups, and
   (c) an acid having a pKa less than 3, as measured at 18° C. in an aqueous solution thereby producing 5-cyanovaleric acid or ester, thereby producing 5-cyanovaleric acid or ester;
   (ii) reducing the 5-cyanovaleric acid or ester to provide 6-aminocaproic acid or ester, and
   (iii) cyclising the 6-aminocaproic acid or ester to provide ε-caprolactam.

9. The process of claim 8 wherein a mixture of branched and linear carbonylation products as obtained in step (i) is used in step (ii) and/or (iii).

10. The process of claim 8 wherein the Group VIII metal is palladium.

11. The process of claim 8 wherein the molar ratio between the ligand (b) and the metal (a) is in the range of 1:1 to 5:1.

12. The process of claim 8 wherein the reaction is carried out at a temperature in the range of about 80 to about 125° C.

13. The process of claim 1 wherein the bidentate ligand is selected from the group consisting of 1,2-bis[(di-tert-penty) phosphinomethyl]benzene and 1,2-bis(di-tertiarybutylphosphinomethyl)benzene.

14. The process of claim 8 wherein the bidentate ligand is selected from the group consisting of 1,2-bis[(di-tert-pentyl) phosphinomethyl]benzene and 1,2-bis(di-tertiarybutylphosphinomethyl)benzene.

15. The process of claim 1 wherein the bidentate ligand of formula (I) is a bisphosphine ligand and $R^1$–$R^4$ represent the same tertiary alkyl groups.

16. The process of claim 1 wherein $R^1$–$R^4$ represent tertiary butyl groups.

17. The process of claim 1 wherein $R^1$–$R^4$ represent tertiary pentyl groups.

18. The process of claim 8 wherein the bidentate ligand of formula (I) is a bisphosphine ligand and $R^1$–$R^4$ represent the same tertiary alkyl groups.

19. The process of claim 8 wherein $R^1$–$R^4$ represent tertiary butyl groups.

20. The process of claim 1 wherein $R^1$–$R^4$ represent tertiary pentyl groups.

* * * * *